США006337021B1

(12) United States Patent
Ma et al.

(10) Patent No.: US 6,337,021 B1
(45) Date of Patent: Jan. 8, 2002

(54) CHIRAL SEPARATION OF ENANTIOMERS BY HIGH-SPEED COUNTERCURRENT CHROMATOGRAPHY

(75) Inventors: Ying Ma, Rockville; Yoichiro Ito, Bethesda, both of MD (US)

(73) Assignee: The United States of America as represented by the Secretary of the Department of Health and Human Services, Washington, DC (US)

(*) Notice: Subject to any disclaimer, the term of this patent is extended or adjusted under 35 U.S.C. 154(b) by 0 days.

(21) Appl. No.: 08/357,845

(22) Filed: Dec. 16, 1994

(51) Int. Cl.[7] ............................................. B01D 15/08

(52) U.S. Cl. ..................... 210/635; 210/657; 210/198.2

(58) Field of Search ................................. 210/635, 656, 210/659, 198.2, 657

(56) References Cited

U.S. PATENT DOCUMENTS

| | | |
|---|---|---|
| 4,414,108 A | 11/1983 | Ito |
| 4,430,216 A | 2/1984 | Ito |
| 4,615,805 A | 10/1986 | Ito |
| 4,849,110 A | 7/1989 | Takata et al. |
| 5,114,589 A | 5/1992 | Shibusawa et al. |
| 5,169,521 A | 12/1992 | Oka et al. |
| 5,169,984 A | 12/1992 | Cahnmann et al. |
| 5,215,664 A | 6/1993 | Kitazume et al. |
| 5,217,608 A | 6/1993 | Conway |
| 5,256,293 A | * 10/1993 | Pirkle ................... 210/198.2 |
| 5,273,656 A | 12/1993 | Anderson |
| 5,290,440 A | * 3/1994 | Pirkle ................... 210/198.2 |
| 5,332,504 A | 7/1994 | Ito et al. ................ 210/635 |
| 5,354,473 A | 10/1994 | Ito et al. |
| 5,449,461 A | 9/1995 | Ito |

OTHER PUBLICATIONS

Ito, Yoichiro, "Cross–Axis Synchronous Flow–Through Coil Planet Centrifuge Free of Rotary Seals for Preparative Countercurrent Chromatography. Part 1. Apparatus and Analysis of Acceleration," *Separation Science and Technology*, 22(8–10):1971–1987 (1987).

Ito, Yoichiro, Cross–Axis Synchronous Flow–Through Coil Planet Centrifuge Free of Rotary Seals For Preparation Countercurrent Chromatography. II. Studies on Phase Distribution and Partition Efficiency in Coaxial Coils, *Separation Science and Technology*, 22(8–10):1989–2009 (1987).

Ito, Y., et al., "Cross–Axis Synchronous Flow–Through Coil Planet Centrifuge for Large–Scale Preparative CounterCurrent Chromatography. I. Apparatus and Studies on Stationary Phase Retention in Short Coils," *J. of Chromatography*, 449:135–151 (1988).

Ito, Y., et al., "Cross–Axis Synchronous Flow–Through Coil Planet Centrifuge for Large–Scale Preparative CounterCurrent Chromatography. II. Studies on Partition Efficiency in Short Coils and Preparative Separations with Multilayer Colis," *J. of Chromatography*, 449:153–164 (1988).

(List continued on next page.)

Primary Examiner—Ernest G. Therkorn
(74) Attorney, Agent, or Firm—Townsend & Townsend & Crew LLP (57) ABSTRACT

Preparative-scale separations of chiral compounds were achieved by high-speed countercurrent chromatography (HSCCC) using a multilayer coil planet centrifuge equipped with a 325 mL capacity column. The separations were performed by two different procedures both utilizing a set of N-(3,5-dintrobenzoyl)-D,L-amino acids as test samples with N-dodecanoyl-L-proline-3,5-dimethylanilide as a chiral selector (Cs). The HSCCC separations were carried out with a two-phase solvent system composed of hexane/ethyl acetate/methanol/water where the chiral selector was added to the organic stationary phase. A second procedure using pH-zone-refining CCC yielded characteristic fused rectangular peaks in which the two isomers were resolved with less than 5% of overlap.

7 Claims, 4 Drawing Sheets

OTHER PUBLICATIONS

Ito, Y., et al., "Cross–Axis Synchronous Flow–Through Coil Planet Centrifuge for Large–Scale Preparative CounterCurrent Chromatography. III. Performance of Large–Bore Coils in Slow Planetary Motion," *J. of Chromatography*, 449:151–162.

Ito, Y. et al., "Improved high–speed counter–current chromatograph with three multilayer coils connected in series. IV. Evaluation of preparative capability with large multilayer coils," *J. of Chromatography*, 538:22–26 (1991).

Ito, Y., et al., "Cross–axis synchronous flow–through coil planet centrifuge (Type XLL) I. Design of the apparatus and studies on retention of stationary phase," *J. of Chromatography*, 538:59–66 (1991).

Ito, Yoichiro, "High–speed Countercurrent Chromatography," *CRC Critical Reviews in Analytical Chemistry*, 17(1):65–143 (1986).

Ito, Yoichiro, "High–Speed Countercurrent Chromatography," *Nature*, 326(6111):419–420 (Mar. 26, 1987).

Conway, Walter D., *Countercurrent Chromatograpy*, VCH Publishers, Inc., New York, pp. 1–115 (1990).

Cahnmann, H.J., et al., "Synthesis and characterization of N–bromoacetyl–3,3', 5–triiodo–L–thyronine," *J. of Chromatography*, 538:165–175 (1991).

Weisz, A., et al., "Complementary use of counter–current chromatography and preparative reversed–phase high–performance liquid chromatography in the separation of a synthetic mixture of brominated tetrachlorofluoresceins," *J. of Chromatography*, 607:47–53 (1992).

Oliveros, L., et al., "Donor–Acceptor Chiral Centrifugal Partition Chromatography: Complete Resolution of Two Pairs of Amino–Acid Derivatives with a Chiral II Donor Selector," *J. Liquid Chromatography*, 17(11):2301–2318 (1994).

Pirkle, W.H., et al., "Use of Intercalative Effects to Enhance Enantioselectivity," *J. Chromatogr.*, 641:11–19 (1993).

Weisz, A., et al., "A New Preparative–Scale Purification Technique: pH–Zone–Refining Countercurrent Chromatography," *J. Am. Chem. Soc.*, 116:704–708 (1994).

* cited by examiner

CHIRAL SEPARATION OF ENANTIOMERS BY HIGH-SPEED COUNTERCURRENT CHROMATOGRAPHY

This invention lies in the field of liquid-liquid partition chromatography, and in particular in the chiral separation of enantiomers using chromatographic techniques.

BACKGROUND OF THE INVENTION

Countercurrent chromatography (CCC) is a form of liquid-liquid partition chromatography which relies on the continuous contact between two immiscible solvents, one of which is mobile relative to the other, in a flow-through tubular column, free of any solid support matrix. The retention time of a solute in the phase contact region of the system is determined by the volume ratio of the solvents, the partition coefficient of the solute between the solvents, and the degree of contact between the solvents. Like other forms of liquid-liquid partition chromatography, one of the solvents serves as a carrier, drawing the solutes from the other solvent and carrying the solutes out of the column in the order of elution. This carrier solvent is thus referred to as the mobile phase, while the other solvent is referred to as the stationary phase, even though it is not strictly stationary in many applications of the method. Solvent mixing, retention of the stationary phase in the column, and solute partitioning all take place in the column by the aid of a suitable acceleration field established by gravity, centrifugal force or both, and the configuration of the column.

Most equipment used for CCC separations involves a coil of column tubing, a portion of which is filled with the stationary phase while the mobile phase is passed through it. By varying the length and diameter of the tubing, CCC has been used for both analytical and preparative separations.

The flow rate of the mobile phase may be varied by varying the field imposed on the column. Units which operate in the presence of a gravitational field only are restricted to slow flow rates, with the resulting separations typically requiring 1 to 3 days, to avoid displacing the stationary phase. A unit which operates in the presence of a centrifugal acceleration field of 40 g or more allows faster flow rates and permits separation times of only a few hours.

Separations by CCC may be performed using any immiscible pair of solvents, provided that the solvents differ in density to at least a slight degree. Both normal-phase and reverse-phase separations may be performed, with the more polar solvent as the stationary phase for normal-phase separations, and the less polar solvent as the stationary phase for reverse-phase separations.

The operational aspects of CCC are similar to the more conventional liquid-liquid chromatography (LLC). Typically, after the immiscible solvent phases are equilibrated relative to one another, the column is filled with the stationary phase. The sample is then injected into the column and elution with the mobile phase is begun. The centrifuge is then started and the eluting fractions are collected. Initially, the fractions are composed of the stationary phase which is displaced from the column. However, once hydrodynamic equilibrium between the phases is achieved, only small portions of the stationary phase will co-elute with the mobile phase. The effluent is continuously monitored with a uv detector and fractionated into test tubes using a fraction collector. The collected fractions are monitored by any of a variety of means including spectroscopic methods and thin-layer chromatography.

Countercurrent chromatographic theory, as well as apparatus for performing the method, are described by Ito, Y., in "Principle and Instrumentation of Countercurrent Chromatography," in *Countercurrent Chromatography: Theory and Practice* Mandava, N. B., and Ito, Y., eds., pp. 79–442 (Marcel Dekker, New York, 1988) and by Conway, W. D., in *Countercurrent Chromatography: Apparatus, Theory and Applications* (VCH, New York, 1990). Most countercurrent chromatographs use a column which is formed into a helical coil. This coil is in turn mounted onto a column holder in various configurations relative to the means for rotating it and relative to the acceleration field that acts on it.

Each column and each type of rotation produce different types of mixing between the solvent phases and are particularly suited for specific separations. However, certain disadvantages to CCC exist.

One disadvantage associated with CCC is the increased peak width associated with increased retention time of the solute. This increased peak width makes detection of the solute more difficult, and requires a larger volume of eluate to be collected and processed in order to obtain a maximum yield of solute. This disadvantage is particularly acute when preparative separations are desired. Nevertheless, increased retention time is desirable in order to avoid coeluting impurities with the solute. Commonly-owned, copending U.S. patent application Ser. No. 07/946,613, filed Sep. 18, 1992, discloses a method for obtaining sharp elution peaks in analytical or semi-preparative CCC without decreasing the retention time of the solute, by adding a peak sharpening agent to either the stationary phase or the sample mixture. When acidic compounds are to be separated, the peak sharpening agent is an acid. When basic solutes are to be separated, the peak sharpening agent is a base.

More recently, an unusually efficient separation of mixtures of acids or bases has been described using a unique modification of the techniques of countercurrent chromatography. See, Ito, et al. U.S. Pat. No. 5,332,504, the disclosure of which is incorporated herein by reference. According to this modification, the two immiscible liquid solutions which are to serve as the stationary and mobile phases, respectively, are modified prior to the performance of the separation by rendering one of the phases acidic and the other basic. Separation of a mixture of acids is then performed in a system in which the acidified solution serves as the stationary phase and the basified solution as the mobile phase. Conversely, separation of a mixture of bases is performed in a system in which the basified solution serves as the stationary phase and the acidified solution as the mobile phase. Individual acid or basic solutes separated by this method elute in contiguous, well-resolved, rectangularly shaped peaks, the solutes eluting in order of their $PK_a$ values and hydrophobicity and the fractions within any single peak being of substantially constant concentration. The combined fractions within each peak differ in pH, successively increasing in the case of a basic mobile phase and successively decreasing in the case of an acidic mobile phase. For this reason, the technique has been referred to as "pH-zone-refining countercurrent chromatography."

A recent modification of pH-zone-refining countercurrent chromatography is carried out in a manner analogous to displacement chromatography. See, commonly-owned, copending U.S. patent application Ser. No. 08/263,924, filed Jun. 21, 1994 and incorporated herein by reference. This method uses a retainer base (acid) in the stationary phase to retain analytes in the column and a displacer acid (base) to elute the analytes in the decreasing (or increasing) order of $pK_a$ and hydrophobicity. The elution produces a train of highly concentrated rectangular solute peaks with minimum overlap. To use pH-zone-refining CCC in a displacement mode, the mobile and stationary phases are switched. Thus, the original eluent becomes a retainer to retain analytes in the stationary phase, and the original retainer acid becomes a displacer to displace the analytes from the stationary phase to the mobile phase at the back of the solute bands.

Displacement countercurrent chromatography and pH-zone-refining countercurrent chromatography (in the normal mode) both entail certain advantages over previously known counter-current chromatography techniques. First, the method permits one to load the sample as a suspension into the separation column. Thus, mixtures of compounds that are only partially soluble in the solvent system can be separated efficiently. In addition, the lack or small degree of elution peak overlap permits one to separate mixtures of greater volume than before in any given column without loss of resolution. For example, columns which are otherwise recommended for separations of mixtures of a certain maximum size can be used for separating mixtures up to ten times that size or greater. Likewise, mixtures containing higher concentrations of the acid or basic solutes can be separated with no loss in resolution. As the concentration of solute increases, the separation simply produces a wider plateau for each solute.

With an increasing demand for optically active compounds, the development of methods for the separation of enantiomers is being intensively pursued. The preparation of optically active compounds has become very important for the development of new biologically active substances containing one or several chiral centers, because many chiral drugs display different activity and toxicity profiles with respect to their absolute configuration.

The direct separation of enantiomers by chromatography is now widely used and a large number of chiral columns using a solid support chiral stationary phase becomes more and more popular and diversified. More than one hundred chiral stationary phases are commercially available allowing many analytical problems to be solved. However, few preparative applications have been reported because of the limited capacity of the standard size columns. Large columns are very expensive.

Compared to the rapid development of optical isomer separation by liquid column chromatography using chiral stationary phases, little work has been reported concerning the separation of optical isomers by countercurrent chromatography. Recently, others have successfully separated D,L-amino acid derivatives by centrifugal partition chromatography. See, Oliveros, et al., *J. Liq. Chromatogr.* 17:2301 (1994). However, this method can only be applied to microgram quantities of samples. Moreover, the chromatographic fractions isolated by Oliveros, et al. were contaminated with substantial amounts of chiral selector and further purification was required. This may also be a problem in other liquid-liquid chromatography techniques.

SUMMARY OF THE INVENTION

The present invention provides methods for the preparative-scale separation of optical isomers of a racemic pair using high-speed countercurrent chromatography (HSCCC). In one embodiment, a chiral selector is held in a liquid stationary phase through which a mobile phase flows, the chromatographic process taking place between the two liquid phases. The separations are carried out with a two-phase solvent system in which the chiral selector is distributed almost exclusively in the stationary phase while the analytes are partitioned between the two phases. The column is first filled with the stationary phase containing the chiral selector, followed by sample injection. The mobile phase is then eluted through the column. A racemic mixture of enantiomers is resolved according to the difference in affinities of the D- and L-forms (or (+) and (−) forms) to the chiral selector. As is a common practice in high performance liquid chromatography (HPLC), the CCC separation can be repeated by successive sample injection without renewing the column contents. The advantage of the present method is derived from the fact that the column contains no solid support and there is no need to immobilize the chiral selector to the solid stationary phase which involves a complicated synthetic process. The liquid stationary phase can hold a large amount of the chiral selector compared to the solid support chiral stationary phase within the conventional chromatographic column. The sample loading capacity and resolution of racemates depend not only on the column volume but also on the concentration of the chiral selector in the stationary phase. Consequently, in HSCCC the chiral separation can be applied in both analytical and preparative scales using the same column only by adjusting the concentration of chiral selector in the stationary phase.

The present invention also provides methods for the preparative-scale separation of optical isomers of a racemic pair using pH-zone-refining countercurrent chromatography.

BRIEF DESCRIPTION OF THE DRAWINGS

In FIG. 1A, the two-phase solvent system was composed of hexane:ethyl acetate:methanol:water (6:4:5:5).

In FIG. 1B, a solvent system of hexane:ethyl acetate:methanol:10 mM HCl (6:4:5:5) was used. For both separations, the apparatus was a multilayer coil high-speed CCC centrifuge with a semipreparative column of 1.6 mm I.D. and 325 mL capacity. N-dodecanoyl-L-proline-3,5-dimethylanilide (30 mM) was added to the upper stationary phase as a chiral selector for both separations. Samples of DNB-Leu (500 mg) were dissolved in 30 mL solvent (15 mL of each phase). Other parameters included a flow rate of 3.0 mL/min in the head to tail elution mode; revolution of 800 rpm; and a stationary phase retention of 65% of the total column capacity.

In FIG. 2A, a sample of (±) DNB-phenylglycine was used.

FIG. 2B shows the separation achieved using a 10 mg sample of (±) DNB-phenylalanine.

FIG. 2C shows the separation of 10 mg each of (±) DNB-valine and (±) DNB-leucine. The samples were each dissolved in 5 mL solvent (2.5 mL of each phase) using a solvent system composed of hexane:ethyl acetate:methanol:0.1 M HCl (6:4:5:5). Other experimental conditions were as follows: Apparatus: Multilayer coil high-speed CCC centrifuge with a semipreparative column of 1.6 mm ID and 325 mL capacity; N-dodecanoyl-L-proline-3,5-dimethylanilide (20 mM) was added in the upper stationary phase as a chiral selector; Flow rate: 3.0 mL/min in the head to tail elution mode; Revolution: 800 rpm; stationary phase retention: 65% of the total column capacity.

FIG. 4 shows the HPLC chromatograms from the separation of (±) DNB-Leucine using pH-zone-refining CCC. The experimental conditions for pH-zone-refining CCC included use of a Multilayer coil high-speed CCC centrifuge with a semipreparative column of 1.6 mm ID and 325 mL capacity; a solvent system composed of methyl t-butyl ether/$H_2O$ with the stationary phase being the upper organic phase to which 20 mM trifluoroacetic acid and 40 mM chiral selector were added. The mobile phase was the lower aqueous phase to which aqueous ammonia was added at 20 mM. A sample size of (±) DNB-Leucine of 2 g was used. See caption for FIG. 2 for the experimental conditions of analytical CCC. Note that the analysis of the fraction from the mixing zone (middle chromatogram) shows three peaks corresponding to (−) DNB-Leu, impurity, and (±) DNB-Leu from left to right.

DETAILED DESCRIPTION OF THE INVENTION

The following abbreviations are used herein: DNB, dinitrobenzoyl; HPLC, high performance liquid chromatography; HSCCC, high-speed countercurrent chromatography; I.D., inside diameter; Leu, leucine; Phe, phenylalanine; Phg, phenylglycine; PTFE, polytetrafluoroethylene; TLC, thin layer chromatography; and Val, valine.

As used herein, the term "racemic" is used to indicate that two enantiomeric forms of a compound are present together in either solid or liquid form. A racemic mixture is optically inactive, but is capable of being separated into dextro- and levorotatory forms. The racemic form of a compound is often denoted as (±), while the optically active enantiomeric forms are denoted separately as (±) and (−). Alternatively, a racemic mixture can be referred to as a dl-mixture or DL, with the separated forms noted as D- and L-.

As used herein, the term "chiral selector" is used to refer to a compound which is chiral (i.e., rotates polarized light) and which interacts more favorably with one member of an enantiomeric pair than with the other member. A chiral selector will typically be one optical isomer of an α-amino acid which is suitably derivatized to provide a compound which partitions more favorably into the stationary liquid phase which is used in a separation. Examples of derivatization include acylation of the α-amino group with a long chain fatty acid (i.e., dodecanoic acid) and/or esterification or amidation of the carboxylic acid residue. In instances in which the chiral selector is partitioned preferably into an organic liquid phase, the carboxylic acid residue will be amidated with a hydrophobic group such as 3,5-dimethylaniline. Other suitable hydrophobic amides, esters and acylated amines can also be prepared. Examples of these are known to those of skill in the art and can be found in, for example, Greene, et al., *Protecting Groups in Organic Synthesis*, Second Edition, Wiley-Interscience, New York, N.Y., (1991), Chapters 5 and 7.

As used herein, the term "separating" means to increase the amount of one component relative to the amounts of other components in a sample mixture. The mixture produced upon "separating" one component will be substantially free from the other components in the sample mixture, but may contain added quantities of solvents.

As used herein, the phrase "immiscible liquid phases" refers to liquids which may be partially miscible, but which separate into two phases having a liquid interface on standing. Typically, the two phases will comprise an organic phase and an aqueous phase. Suitable organic solvents include diethyl ether, hexane, ethyl acetate, methanol, methyl t-butyl ether, and acetonitrile.

As used herein, the term "identifying" means determining by spectroscopic means such as UV detection, refractive index detection, mass spectroscopy, and IR detection whether the desired compound is present in a particular sample or eluted fraction. Compounds may also be "identified" by a comparison of their elution times using HPLC.

The method of the present invention utilizes a countercurrent chromatographic centrifuge which may be any of the centrifuges generally used in other modes of countercurrent chromatography. A variety of these centrifuges have been described by Ito, Y., in "Principle and Instrumentation of Countercurrent Chromatography," in *Countercurrent Chromatography: Theory and Practice* Mandava, N. B., and Ito, Y., eds., pp. 79–442 (Marcel Dekker, New York, 1988) and by Conway, W. D., in *Countercurrent Chromatography: Apparatus, Theory and Applications* (VCH, New York, 1990).

Countercurrent chromatography utilizes the hydrodynamic behavior of two immiscible solvent phases mixing in a column to effect the separation of a solute from other components in a sample.

For any of the methods of the present invention, any mixture of solvents which forms two phases on standing may be used. The phases may each be independently composed of organic solutions or aqueous solutions. In a preferred embodiment, one phase is composed of one or more organic solvents and the other phase is substantially aqueous. When chromatography is conducted with the aid of a centrifuge, preferred solvents are those which form two phases having a difference in density of at least 0.05 g/mL. The phases may be equilibrated relative to one another either prior to or during chromatography. In those methods using an acidified or basified liquid phase(s), the two phases may be equilibrated prior to acidifying or basifying the separate phases. When a basic aqueous phase is used as a mobile phase for separation of acidic solutes, the phases may be equilibrated after the aqueous phase is made basic. Similarly, when an acidic aqueous phase is used as a mobile phase for the separation of basic solutes, the phases may be equilibrated after the aqueous phase is made acidic. In a preferred embodiment, the phases are equilibrated in their neutral form by shaking them together and then allowing them to separate prior to charging the column with the stationary phase. When the phases are equilibrated in their neutral form, the stationary phase may be acidified (for separation of acidic solutes) or basified (for separation of basic solutes) prior to charging the chromatography column.

The selection of the solvent system for chiral separations using HSCCC is primarily based on the partition coefficients (K) between the two phases of both the chiral selector and the analyte of interest. Preferably, the chiral selector will be distributed mainly into the stationary phase, whereas the analytes should have K values of about 0.3 to 1.0 so that they are rather evenly distributed between the two phases. In a preferred embodiment, the solvent system is composed of hexane, ethyl acetate, methanol and water. More preferably, the solvent system is composed of hexane, ethyl acetate, methanol and 10 mM HCl.

The selection of the solvent system for chiral separations using pH-zone-refining CCC will be as described in U.S. Pat. No. 5,332,504. Briefly, the degree of acidity and basicity of the two phases is not critical. In most applications, best results will be achieved by using an acidic phase with a pH below about 4 and preferably below about 3. Similarly, the basic phase will in most cases have a pH above about 8 and preferably above about 9. The use of a more basic mobile phase will result in shorter elution times for acidic compounds. Similarly, a more acidic mobile phase will reduce the elution times of basic samples.

The motions which are applied to a CCC column are best described as corresponding to a solar system. In particular, a coiled column may undergo rotation about one or more axes. Solar coaxial motion is found when the coiled column is rotated about the axis of the coil. When the coil is mounted with its axis parallel and offset from a second axis, and the column is rotated only about the second axis, the rotation is termed solar satellite or solar eccentric motion. Planetary motion is provided when rotation occurs about two axes. When a coiled column is rotated about its own axis and also rotated about a second parallel axis, the motion is termed planetary coaxial motion. When a coiled column is rotated about a first external axis parallel to the axis of the coiled column, and the first external axis is simultaneously revolving about a second external parallel axis, the motion is termed planetary satellite or planetary eccentric motion.

In addition to configurations having parallel axes, there are also configurations in which the column axis is inclined or skewed relative to the external axes. Another type of planetary motion results when the two axes about which rotation occurs are orthogonal to one another. Methods utilizing this type of configuration are termed cross-axis CCC.

The columns employed in CCC are equally diverse. The majority are helical, but may vary in the material of fabrication, length, width, pitch of its winding, and mounting onto a column holder. Modern columns are typically constructed of polytetrafluoroethylene tubing which is capable of maintaining its shape and integrity while being exposed to a strong acceleration field. The inside diameter of the tubing is typically between 0.75 and 3 mm. While a single-layer coil may involve only a few meters of tubing, a multi-layer coil might contain more than 100 m of the tubing. Columns to be used for analytical purposes typically have an inside diameter which is more narrow and a length which is longer than a column used for preparative purposes. Additionally, helical columns may be either right-handed or left-handed. The handedness of the coils are determined by the direction in which the coils are wound onto a spool-shaped column holder. The helical column may be either a single layer or multilayer coil. For another column shape, the tubing may be wound onto a flexible core which is in turn coiled onto the column holder to produce a toroidal coil. Yet another type of column is a single layer spiral in which the tubing is wound in one layer onto a core and upon itself. The columns are further equipped with flow tubes which provide for the introduction of sample and mobile phases using an external pump. The tubes further allow the eluate to be collected using an automated fraction collector.

The present invention can be used with any of the columns and motions employed for CCC. The preferred apparatus is a high-speed countercurrent chromatographic centrifuge having a multilayer-coil separation column. The preferred motion is planetary motion (either coaxial or eccentric). Particularly preferred is synchronous planetary motion in which the number of revolutions about each of the two axes of rotation is the same within a particular period of time. The synchronous planetary motion provided by the centrifuge performs two functions. First, the synchronous rotation of the column holder constantly unwinds the twist of the flow tubes caused by revolution. This permits continuous elution through the rotating coil without the use of a conventional rotary seal device, which can be a potential source of leakage and contamination of collected fractions. Additionally, when the coiled column is coaxially mounted about the coil holder, the planetary motion of the holder unilaterally distributes two solvent phases in the column in such a way that one phase occupies the head side, and the other phase occupies the tail side of the coil. This head-tail relationship refers to the Archimedean screw force acting on the rotating coil, where all objects of different density are driven from the tail portion of the coil toward the head of the coil. This hydrodynamic phenomenon can be utilized for performing CCC in two ways. The coil can be entirely filled with a first liquid phase and eluted with the second liquid phase from the tail toward the head. Alternatively, the coil can be filled with the second liquid phase followed by elution with the first liquid phase from the head toward the tail. In either case the hydrodynamic phenomenon facilitates rapid movement of the mobile phase through the stationary phase, yielding extremely high retention of the stationary phase in the coil.

In one group of embodiments, the present inventive method is used to separate the enantiomers of a racemic compound mixture from each other in a sample mixture using HSCCC. Two immiscible solvent phases are equilibrated relative to one another to yield a two-phase mixture. A countercurrent chromatographic centrifuge column is then charged with a first liquid phase of the mixture. The first liquid phase is charged with a chiral selector, and the sample mixture containing the racemic compound to be separated is introduced into the column. Alternatively, the chiral selector is added to the stationary phase (first liquid phase) prior to its introduction to the column. The centrifuge is started and the second liquid phase, or mobile phase, is passed through the column. Fractions containing the various components of the mixture are eluted, collected and identified.

The liquid phases are each independently an organic phase or an aqueous phase. In preferred embodiment, the first liquid phase is an organic phase and the second liquid phase is an aqueous phase. In a further preferred embodiment, the first liquid phase is an organic phase and the second liquid phase is an acidic aqueous phase.

As noted above, the chiral selector is typically selected so that it is retained primarily in the first liquid phase (the stationary phase). In those applications in which the stationary phase is an organic phase, the chiral selector will be a hydrophobic compound, such as a derivatized amino acid, preferably N-dodecanoyl-L-proline-3,5-dimethylanilide. Alternatively, in separations in which the stationary phase is aqueous, the chiral selector will be more hydrophilic. The concentration of chiral selector which is used is typically from about 0.1 to about 200 mM, preferably from about 1.0 to about 100 mM, and more preferably from about 10 to about 50 mM.

The amount of a racemic compound which is to be separated into its two enantiomers will typically be from about 1 mg to about 1 kg, preferably from about 0.05 grams to about 50 grams, more preferably from about 0.5 to about 10 grams, and still more preferably from about 1.0 to about 5.0 grams.

In another group of embodiments, the present inventive method is used to separate the enantiomers of a racemic acidic compound mixture from each other in a sample mixture using pH-zone-refining CCC. In this method, a chiral selector and an acid are added to a first liquid phase of two pre-equilibrated immiscible liquid phases. A countercurrent chromatographic centrifuge column is then charged with the first liquid phase. Base is then added to the second liquid phase of the two pre-equilibrated immiscible liquid phases to form a basic mobile phase. The racemic acidic compound mixture is introduced into the injection port of the countercurrent chromatographic centrifuge column and the basic mobile phase is passed through the countercurrent chromatographic centrifuge column to elute, in a separated form, the (+) enantiomer and the (−) enantiomer of the racemic acidic compound.

The amount of racemic compound which can be separated into its component enantiomers using this method is, as above, from about 1 mg to 1 kg quantities. Preferably, the amount to be separated is from about 0.05 to 50 grams, and more preferably from about 1.0 to about 10 grams. In a still further preferred embodiment, the method can be used for separating a quantity of an acidic compound in a suspension.

As above, the liquid phases are each independently an organic phase or an aqueous phase. In a preferred embodiment, the first liquid phase is an organic phase and the second liquid phase is an aqueous phase. In a further preferred embodiment, the first liquid phase is made acidic with an organic acid which is either acetic acid, trifluoroacetic acid, propionic acid or butanoic acid. In a still further preferred embodiment, the first liquid phase is made acidic with trifluoroacetic acid. In another preferred embodiment, the second liquid phase is made basic with either ammonia or NaOH, more preferably ammonia.

The chiral selector used in this group of embodiments is also selected so that it is retained primarily in the first liquid phase (the stationary phase). In those applications in which the stationary phase is an organic phase, the chiral selector will be a hydrophobic compound, such as a derivatized amino acid, preferably N-dodecanoyl-L-proline-3,5-dimethylanilide.

In yet another group of embodiments, the present inventive method is used for separating a quantity of the (+) and (−) enantiomers of a racemic basic compound mixture from each other using pH-zone-refining CCC. In these embodiments, as above, two immiscible liquid phases are equilibrated relative to one another, then separated. A countercurrent chromatographic centrifuge column is charged with a first liquid phase which is made basic either prior to or following its introduction into the column. The first liquid phase is also charged with a chiral selector. The mixture containing a quantity of a racemic basic compound to be separated is then introduced into the column. The centrifuge is started and the second liquid phase, which has previously been made acidic, is passed through the column. Fractions containing the various components of the mixture are eluted, collected and identified.

As above, the liquid phases are each independently an organic phase or an aqueous phase. In a preferred embodiment, the first liquid phase is an organic phase and the second liquid phase is an aqueous phase. The liquid phases will typically be acidified or basified as required using the acids and bases described above. Additionally, the chiral selector used will be as described above for the racemic acidic compound mixture. In another preferred embodiment, pH-zone-refining countercurrent chromatography can be conducted on a preparative scale using 1 mg to 1 kg of the mixture containing the racemic basic compound which is to be separated. In a still further preferred embodiment, the method can be used for separating a quantity of a racemic basic compound in a suspension.

The following examples are offered by way of illustration and are not meant to limit the scope of the invention.

EXAMPLES

Apparatus

A commercial model (Ito multilayer coil separator/extractor, P.C. Inc., Potomac, Md., USA) of the high-speed CCC centrifuge was used throughout the present studies. The detailed design of the apparatus was given elsewhere (U.S. Pat. No. 4,430,216). The apparatus holds a multilayer coil separation column and a counterweight symmetrically at a distance of 10 cm from the central axis of the centrifuge. The column holder is equipped with a plastic planetary gear which is engaged to an identical stationary sun gear mounted around the central axis of the apparatus. This gear arrangement produces the desired planetary motion to the column holder, i.e. rotation about its own axis and revolution around the centrifuge axis in the same direction at the same rate. This planetary motion also prevents the flow tubes from twisting during revolution, thus permitting the elution of the mobile phase through the column without the use of rotary seals.

The separation column consists of a single piece of 1.6 mm ID, 160 m long PTFE (polytetrafluoroethylene) tubing (Zeus Industrial products, Raritan, N.J., USA) wound around the column holder hub with 16 layers and 325 mL capacity. Each terminal of the column was connected to a flow tube (0.85 mm ID PTFE) (Zeus Industrial Products) by the aid of a set of tube connectors (Upchurch Scientific Co., Oak Harbor, Wash., USA) which were rigidly mounted on the holder flange. A narrow-bore PTFE tube (0.3 mm ID×5 m)(Zeus Industrial Products) was placed at the outlet of the column to stabilize the effluent flow, thus facilitating the recording the elution curves.

The speed of the apparatus was regulated with a speed controller (Bodine Electric Company, North Chicago, Ill., USA).

Reagents

Methanol was glass-distilled chromatographic grade (Baxter Healthcare Corporation, Muskegon, Mich., USA). HPLC grade of hexane and ethyl acetate, and reagent grade of sodium hydroxide and hydrochloric acid were purchased from Fisher Scientific Company (Fair Lawn, N.J., USA). Dinitrobenzoyl(DNB)-leucine, DNB-phenylglycine and 3,5-DNB chloride were obtained from Aldrich Chemical Co., (Milwaukee, Wis., USA). DL-proline, DL-valine, DL-phenylalanine, 2-ethoxy-1-ethoxycarbonyl-1,2-dihydrofuran (EEDQ), dodecanoyl chloride, 3,5-dimethylaniline were purchased from Spectrum Chemical Mfg. Corp. (New Brunswick, N.J., USA).

Synthesis of Chiral Selector

N-dodecanoyl-L-proline: L-proline (11.6 g, 0.1 mol) was dissolved in 150 mL of 1 M NaOH solution and cooled in an ice both. To this solution dodecanoyl chloride (24.1 g or 0.11 mol) and 200 mL of 1 M NaOH solution were added simultaneously over a period of 20 min. The solution was stirred at room temperature for 45 min and acidified with concentrated HCl (pH 2–3). The solution was extracted with diethyl ether and the organic phase was washed with 12% NaCl solution. The organic phase was then dried over sodium sulfate and evaporated to provide 30 g of N-dodecanoyl-L-proline as an oil (100% yield) which was carried on without purification.

N-dodecanoyl-L-proline-3,5-dimethylanilide: To 400 mL of a THF solution containing 13.0 g (0.11 mol) of freshly distilled 3,5-dimethylaniline and 30 g (0.1 mol) of N-dodecanoyl-L-proline, was added 200 mL of THF containing 25.2 g (0.1 mol) of EEDQ at room temperature. The mixture was kept at room temperature for 24 hr and the solvent was evaporated. The residue was redissolved in dichloromethane and washed with 1% orthophosphoric acid, 0.2 M NaOH and then distilled water. The resulting solution was dried over sodium sulfate, filtered and evaporated. Recrystallization of the residue from ethanol-water gave 35.0 g (87% yield) of white solid.

Another chiral selector which is useful for the separation of naproxen isomers is N-(2', 6'-dimethylpiperidine)-6-methoxy-α-methyl-2-naphthanlene ethanamide. Synthesis of this chiral selector was carried out as follows:

(S)-naproxen, (S-(+)-methoxy-α-methyl-2-naphthalene acetic acid), (2.30 g, 10 mmol) was dissolved in 50 mL of methylene chloride and 2 mL of oxalyl chloride was added. After 3 hours, the solution was evaporated to dryness and the remaining crystalline solid was dried under vacuum for 3 hours. The solid was dissolved in 100 mL of dry methylene chloride and cooled in an ice-water bath. 2,6-dimethylpiperidine (13.5 mL, 100 mmol) was added slowly with stirring, and the mixture was kept at room temperature for 2 hours. The resulting mixture was washed successively with 1M HCl (100 mL), 1% NaOH (100 mL) and water, then dried over magnesium sulfate. Removal of solvent under reduced pressure provided 3.2 g (98% yield) of N-(2', 6'-dimethylpiperidine)-6-methoxy-α-methyl-2-naphthanlene ethanamide.

Synthesis of Analytes (±) N-(3,5-dinitrobenzoyl)amino acids: An appropriate amount of racemic amino acid (23 mmol) was dissolved in 50 mL of 1M NaOH solution and cooled in an ice-bath. To this solution 3,5-dinitrobenzoyl chloride (5.3 g, 23 mmol) and 50 mL of 1M NaOH solution were added simultaneously over a period of 20 min. The resulting solution was stirred at room temperature for 90 min and acidified with concentrated HCl (pH 2–3). The resulting solid was collected by filtration and washed with water. Recrystallization of the solid from ethanol-water gave the corresponding DNB-amino acid.

Preparation of Solvent Phases and Sample Solutions

The solvent pair was prepared as follows: hexane, ethyl acetate, methanol and distilled water (or dilute HCl solution) were thoroughly equilibrated in a separatory funnel at room temperature and the two phases were separated. The chiral selector (N-dodecanoyl-L-proline-3,5-dimethylanilide, 10–60 mM) was added to the upper organic phase which was then used as the stationary phase. The lower aqueous phase was used as the mobile phase.

Sample solutions were prepared by dissolving a set of DNB-amino acids in 10–50mL of solvent typically consisting of about equal volumes of upper organic and lower aqueous phases. The solution was sonicated for several minutes before injecting into the column.

Separation Procedure

In each separation, about 150 mL of the organic stationary phase free of chiral selector was first pumped into the column followed by 200 mL of the same organic phase but containing the chiral selector at a desired concentration. The sample solution was then injected through the sample port and the aqueous mobile phase was eluted through the column in the head to tail elution mode at a flow rate of 3.0 mL/min (Rainin Metering Pump: Rainin Instruments Co. (Emeryville, Calif., USA)) while the apparatus rotated at 800 rpm. The effluent from the column was continuously monitored by absorbance at 254 nm (Uvicord S, LKB Instruments, Bromma/Stockholm, Sweden) and collected at 3.0 mL/tube (Ultrorac Fraction Collector, LKB Instruments). After all peaks were eluted, the centrifuge run was terminated, and the column contents were collected into a graduated cylinder by connecting the inlet of the column to a nitrogen line at 80 psi. The retention of the stationary phase relative to the total column capacity was computed from the volume of the stationary phase collected from the column (65–80%).

Analysis of CCC Fractions

CCC fractions were analyzed by TLC on Kieselgel 60 F254 with heptane:ethyl acetate (1:1) as eluent. The enantiomer purity of the DNB-amino acids was determined by optical rotation and circular dichroism.

Example 1

This example illustrates the separation of (±)-DNB-Leucine using HSCCC.

Figure 1:
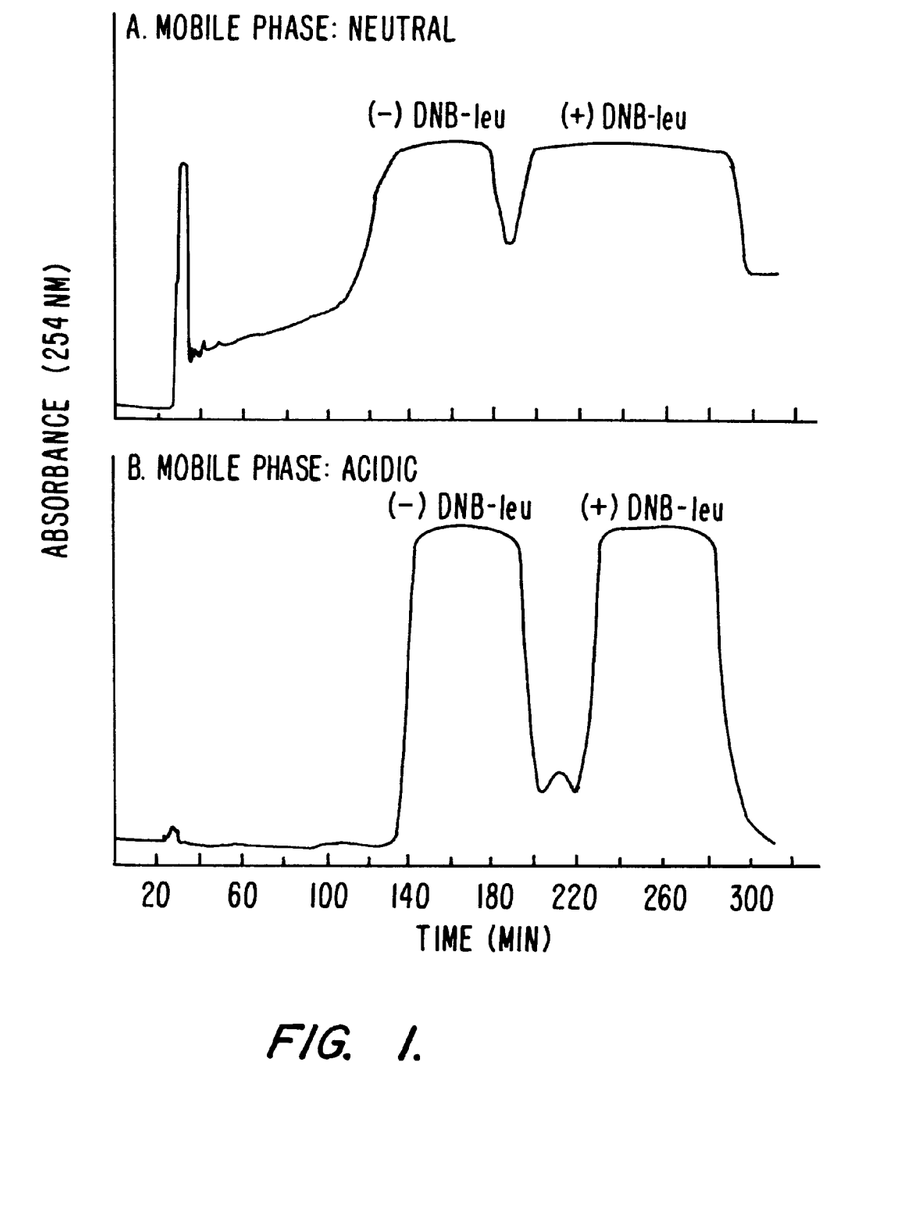
FIG. 1 shows two HPLC chromatograms from chiral separations of (±) 3,5-dinitrobenzoyl-leucine by HSCCC.

Complete separation of 500 mg of N-(3,5-dinitrobenzoyl)-leucine was achieved by HSCCC using a multilayer coil planet centrifuge equipped with a 325 mL capacity column (FIG. 1). The separation was carried out with a two-phase solvent system composed of hexane, ethyl acetate, methanol and water (A) or 10 mM HCl (B) (6:4:5:5, by volume) where N-dodecanoyl-L-proline-3,5-dimethylanilide was added in the upper stationary phase as a chiral selector. The mechanism of the separation is similar to that recently described by Pirkle et al., *J. Chromatogr.*, 641:11 (1993) in which the chiral selector was chemically bound to the surface of silica gel. The chromatogram (A) obtained by the neutral mobile phase shows skewed peaks which lead to incomplete peak resolution. The peak resolution was substantially improved by using an acidic mobile phase (B) because at the lower pH all analyte molecules are protonated and distributed by a uniform K value according to the linear isotherm.

In HSCCC the selection of the solvent system for chiral separation is mainly based on the partition coefficients (K) of both the chiral selector and analytes. The partition coefficient (K) is defined as $C_s/C_m$, where $C_s$ is the concentration in the stationary phase and $C_m$ is the concentration in the mobile phase. The chiral selector should have a large K value so that it is unilaterally distributed to the organic stationary phase whereas the analytes should have K values of near unity to be rather evenly partitioned between the two phases. In the present example this requirement was fulfilled by binding a dodecanoyl group to the L-proline-3,5-dimethylanilide to increase the hydrophobicity of the selector molecule. In the solvent system composed of hexane, ethyl acetate, methanol and 10 mM HCl (6:4:5:5) used in the above separation, the partition coefficient of the chiral selector is as large as 45.1 while DNB-Leucine has a partition coefficient of 1.3.

Contamination of the chiral selector in the eluted fractions was further prevented by filling the column only partially with the stationary phase containing the chiral selector while leaving the end of the column space with the same phase free of the chiral selector. In this way a small amount of the chiral selector carried by the flowing mobile phase is absorbed into the stationary phase near the end of the column.

Example 2

This example illustrates the separations which are achieved using racemic mixtures of DNB-phenylglycine, -phenylalanine, -leucine, and -valine and correlates the amount of separation with the nature of the side chain and the partition coefficient, K. The partition coefficient is calculated as the concentration of the analyte in the stationary phase ($C_s$) divided by the concentration of the analyte in the mobile phase ($C_m$).

Figure 2:
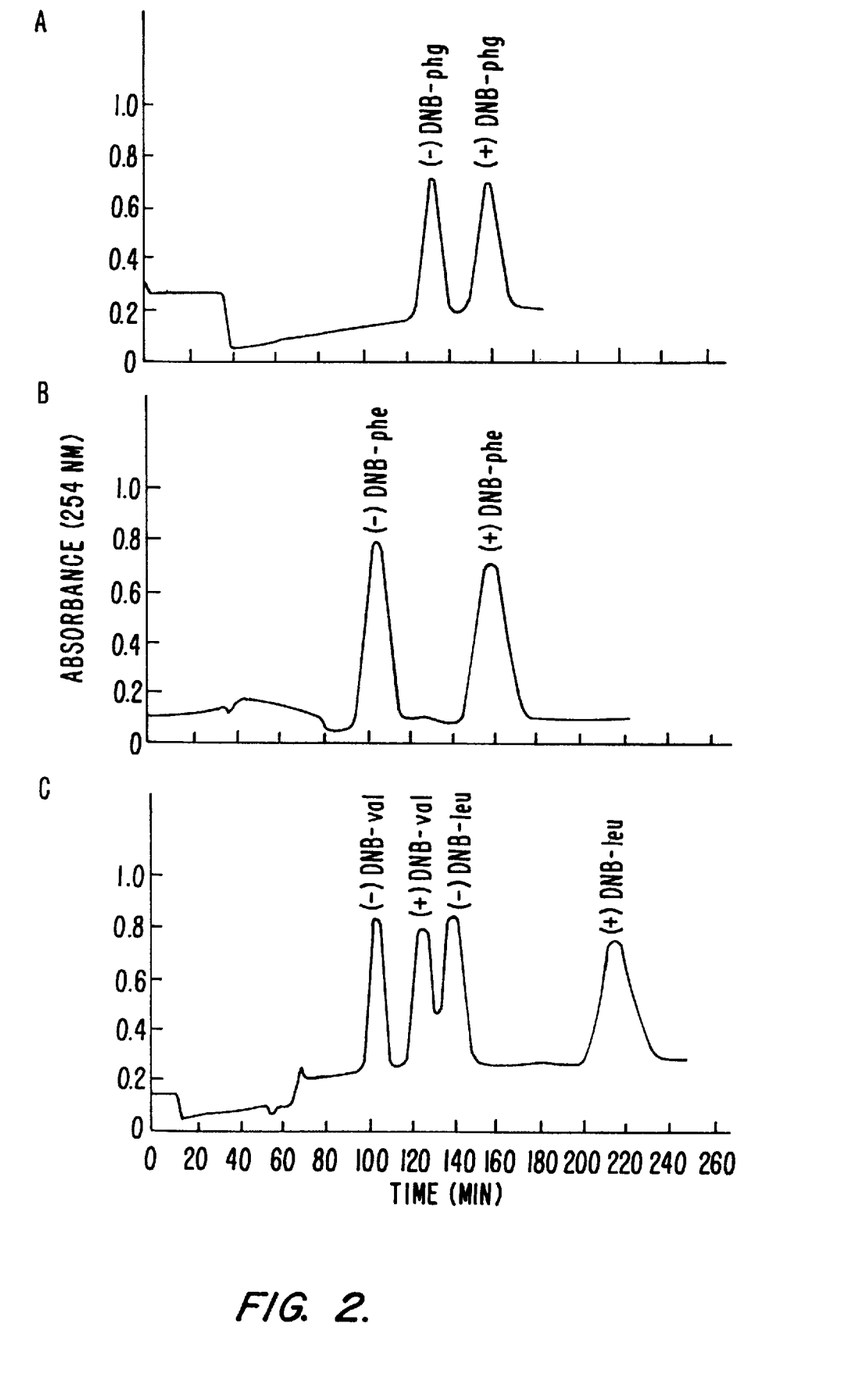
FIG. 2 shows chromatograms from the chiral separation of a set of DNB-amino acids by HSCCC.

The enantiomers of the homologous series of DNB-amino acids were separated with the same system on an analytical scale (10 mg) in order to investigate the mechanism of enantioselectivity of the chiral selector in HSCCC (FIG. 2). The separations were performed in the solvent system composed of hexane/ethyl acetate/methanol/10 mM HCl (6:4:5:5) where N-dodecanoyl-L-proline-3,5-dimethylanilide were again used as a chiral selector in the upper stationary phase. Chromatograms A and B were obtained by injecting the racemic mixture of DNB-Phg and DNB-Phe, respectively, and chromatogram C by simultaneous injection of the racemic mixtures of DNB-Leu and -Val. The separation was repeated by successive sample injection without renewing the column contents. The results indicate the enantioselectivity of DNB-amino acids is related to the side chain (R) of the molecule (Table 1). The chromatographic separation factor, which is determined from the ratio of retention time between two enantiomers (here the retention time is the time required to elute the analytes after the solvent front has emerged) increases with the increasing size of R, while it also relates to hydrophobicity of the solvent system and the concentration of chiral selector in stationary phase.

TABLE 1

Separation Factors of Enantiomers of DNB-Amino Acids

| Sample | R | $K = C_s/C_m$* | Separation factor |
| --- | --- | --- | --- |
| DNB-Leucine | —CH$_2$CH(CH$_3$)$_2$ | 1.24 | 1.76 |
| DNB-Valine | —CH(CH$_3$)$_2$ | 0.78 | 1.38 |
| DNB-Phenylalanine | —CH$_2$C$_6$H$_5$ | 1.08 | 1.71 |
| DNB-Phenylglycine | —C$_6$H$_5$ | 0.93 | 1.25 |

*K indicates the partition coefficient of enantiomers before the chiral selector is added to the solvent system.

Example 3

This example illustrates the effect of the chiral selector concentration on the separation of (±)-DNB-Leucine.

Figure 3:
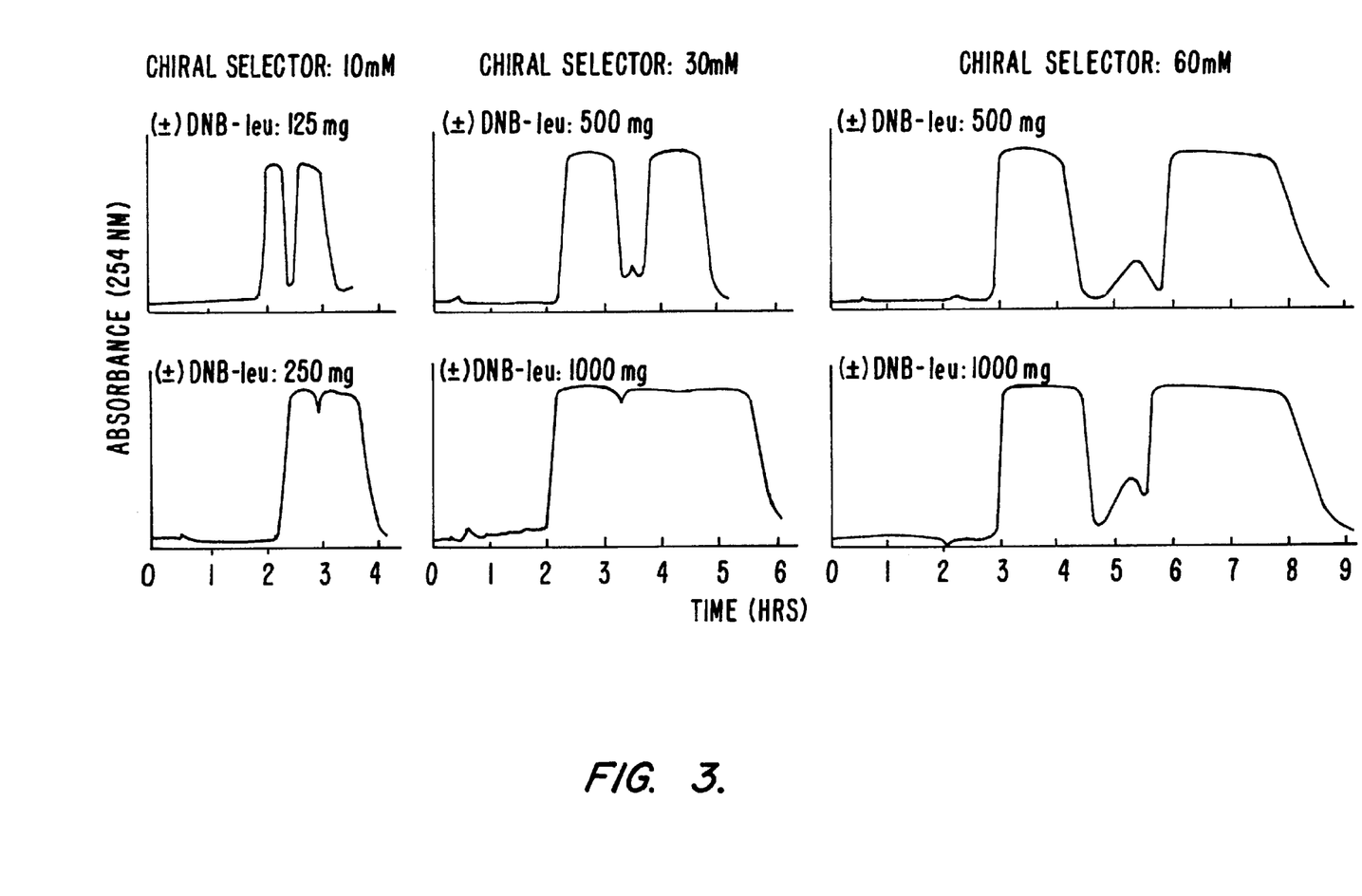
FIG. 3 shows six HPLC chromatograms which illustrate the effect of varying the amount of the chiral selector in the stationary phase for the chiral separations of (±) DNB-leucine using HSCCC. The apparatus used was a Multilayer coil highspeed CCC centrifuge with a semipreparative column of 1.6 mm ID and 325 mL capacity. The solvent system was composed of hexane/ethyl acetate/methanol/10 mM HCl (6:4:5:5). N-dodecanoyl-L-proline- 3,5-dimethylanilide was added to the upper stationary phase as a chiral-selector at concentrations of 10 mM (A), 30 mM (B) and 60 mM (C). Samples of (±)DNB-Leu were (A) 125 mg and 250 mg, (B & C) 500 mg and 1000 mg dissolved in 10–45 mL of solvent (equal volumes of each phase). Other parameters were as described under FIG. 1.

The sample loading capacity of the present method was investigated with the separation of DNB-leu by varying the concentration of the chiral selector in the stationary phase. As shown in FIG. 3, concentrations of the chiral selector at 10, 30 and 60 mM in the stationary phase were examined in the same solvent system composed of hexane/ethyl acetate/methanol/10 mM HCl (6:4:5:5). The result indicated that the sample loading capacity is largely determined by the concentration of the chiral selector in the stationary phase: The higher the concentration of the chiral selector, the better peak resolution is obtained.

These results clearly demonstrate an important advantage of HSCCC in the separation of enantiomers. The same column can be applied to both analytical and preparative scale separations by choosing different concentrations of chiral selector in the stationary phase.

Example 4

This example illustrates the separation of (±)-DNB-Leucine using pH-zone-refining countercurrent chromatography.

pH-Zone-refining CCC is a powerful preparative method comparable to displacement chromatography. The method yields a succession of highly concentrated rectangular solute peaks with minimum overlap where impurities are concentrated at the peak boundaries. See, U.S. Pat. No. 5,332,504, incorporated herein by reference.

Figure 4:
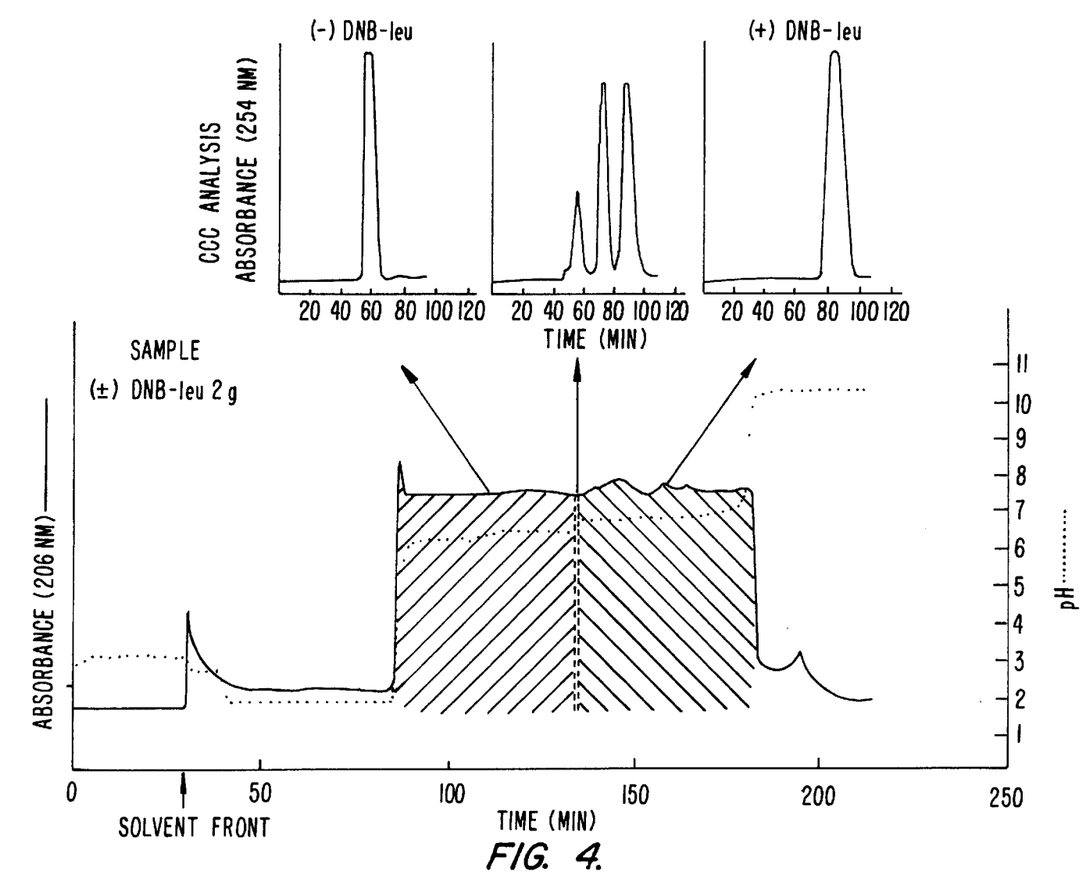

The separation of chiral compounds using pH-zone-refining CCC was performed with a binary two-phase solvent system composed of methyl t-butyl ether and water. After the two phases were separated, proper amounts of a retainer acid (trifluoroacetic acid, 20 mM) and the chiral selector (N-dodecanoyl-L-proline-3,5-dimethylanilide, 40 mM) were added to the organic stationary phase and an eluent base (ammonia) was added to the aqueous mobile phase. The column was first completely filled with the organic stationary phase followed by injection of the sample solution containing 2 g of (±) DNB-leu. The mobile phase was then eluted through the column while the apparatus was rotated at 800 rpm. The effluent from the outlet of the column was continuously monitored with a UV monitor (Uvicord S) at 206 nm and fractionated into test tubes (3 mL/tube). FIG. 4 shows a typical chromatogram obtained by the present method. The analyte was eluted in a single rectangular peak which is evenly divided by two pH zones. The separation was completed in about 3 hours. Peak fractions were analyzed by analytical scale CCC as described earlier. The results showed that the first part was almost entirely composed of (−) DNB-leu and the second part from (±) DNP-leu which the middle portion of the peak contained both isomers and an impurity as shown in the upper portion of the diagram (FIG. 4). The mixing zone of the two peaks is estimated less than 5% of each peak.

Compared with the standard CCC technique described earlier, the pH-zone-refining CCC technique enables the separation of larger amounts of the sample in a shorter period of time. In addition, the method uses a relatively polar solvent system which can hold a chiral selector for a much longer period of time, thus reducing the risk of its contaminating the effluent fractions.

The overall results of our studies indicate that the present method can be utilized for chiral separation of gram quantities of DNB-amino acids. The method may be extended to the separation of various chiral compounds using appropriate chiral selectors.

The above description is illustrative and not restrictive. Many variations of the invention will become apparent to those of skill in the art upon review of this disclosure. Merely by way of example a variety of analytes, chiral selectors, liquid phases and mixtures, and other materials may be used without departing from the scope of the invention. The scope of the invention should, therefore, be determined not with reference to the above description, but instead should be determined with reference to the appended claims along with their full scope of equivalents.

What is claimed is:

1. A method for separating a quantity of the (+) and (−) enantiomers of a racemic compound mixture from each other using high-speed countercurrent chromatography, comprising:

(a) adding a chiral selector to a first liquid phase of two pre-equilibrated immiscible liquid phases and charging a countercurrent chromatographic centrifuge column with said first liquid phase, thereby producing a countercurrent chromatographic centrifuge column charged with said chiral selector and said first liquid phase;

(b) introducing said racemic compound mixture into said countercurrent chromatographic centrifuge column thus charged with said chiral selector and said first liquid phase; and (c) passing a second liquid phase through said countercurrent chromatographic centrifuge column thus charged with said mixture, said chiral selector and said first liquid phase, to elute said (+) enantiomer and said (−) enantiomer from said countercurrent chromatographic centrifuge column, wherein said quantity is from 1 mg to 1 kg.

2. The method in accordance with claim 1 wherein said first liquid phase is an organic phase and said second liquid phase is an aqueous phase.

3. The method in accordance with claim 1 wherein said first liquid phase is an organic phase and said second liquid phase is an acidic aqueous phase.

4. The method in accordance with claim 1 wherein said first liquid phase is an aqueous phase and said second liquid phase is an organic phase.

5. The method in accordance with claim 1 wherein said chiral selector is N-dodecanoyl-L-proline-3,5-dimethylanilide.

6. The method in accordance with claim 1 wherein said column is a helical column.

7. The method in accordance with claim 1 wherein said chiral selector is present in said first liquid phase at a concentration of from 0.1 to 200 mM.

* * * * *